United States Patent [19]

Stanley

[11] Patent Number: 5,116,576
[45] Date of Patent: May 26, 1992

[54] DEVICE FOR ANALYTICAL DETERMINATIONS

[75] Inventor: Christopher J. Stanley, Cambridgeshire, United Kingdom

[73] Assignee: Scientific Generics Limited, Cambridge, United Kingdom

[21] Appl. No.: 548,971

[22] PCT Filed: Dec. 7, 1988

[86] PCT No.: PCT/GB88/01071
§ 371 Date: Aug. 2, 1990
§ 102(e) Date: Aug. 2, 1990

[87] PCT Pub. No.: WO89/05457
PCT Pub. Date: Jun. 15, 1989

[30] Foreign Application Priority Data

Dec. 8, 1987 [GB] United Kingdom ............... 8728639

[51] Int. Cl.$^5$ ................. G01N 21/00; G01N 33/561; C12M 1/34
[52] U.S. Cl. ........................... 422/55; 422/58; 422/61; 422/68.1; 435/287; 435/291; 436/518
[58] Field of Search .............. 422/55, 61, 87, 102, 422/68.1, 58; 435/291, 287; 436/45, 44, 46, 43, 518

[56] References Cited

U.S. PATENT DOCUMENTS

| | | |
|---|---|---|
| 3,723,064 | 3/1973 | Liotta . |
| 3,825,410 | 7/1974 | Bagshawe . |
| 3,933,594 | 1/1976 | Milligan et al. ............... 435/287 |
| 4,770,853 | 9/1988 | Bernstein ....................... 422/61 |
| 4,842,995 | 6/1989 | Iaccheri et al. ................ 422/61 |
| 4,898,832 | 2/1990 | Klose et al. ................... 436/45 |
| 4,916,078 | 4/1990 | Klose et al. ................... 436/45 |

FOREIGN PATENT DOCUMENTS

| | | |
|---|---|---|
| 0052769 | 6/1982 | European Pat. Off. . |
| 0174247 | 3/1986 | European Pat. Off. . |
| 0279574 | 8/1988 | European Pat. Off. . |
| 1598224 | 7/1970 | Fed. Rep. of Germany . |

Primary Examiner—Jill Johnston
Assistant Examiner—William Chan
Attorney, Agent, or Firm—Bacon & Thomas

[57] ABSTRACT

A device for carrying out an analytical determination which comprises an assay cassette and a transport body which is adapted for location in the assay cassette, the assay cassette having a plurality of discrete reagent chambers which are separated from one another by a separation arrangement which, in use, is ruptured or opened by the transport body. An assay cassette is also described which includes a signal detection chamber that is separated from the final reagent chamber by a separation arrangement which, in use, is ruptured or opened by the transport body.

22 Claims, 6 Drawing Sheets

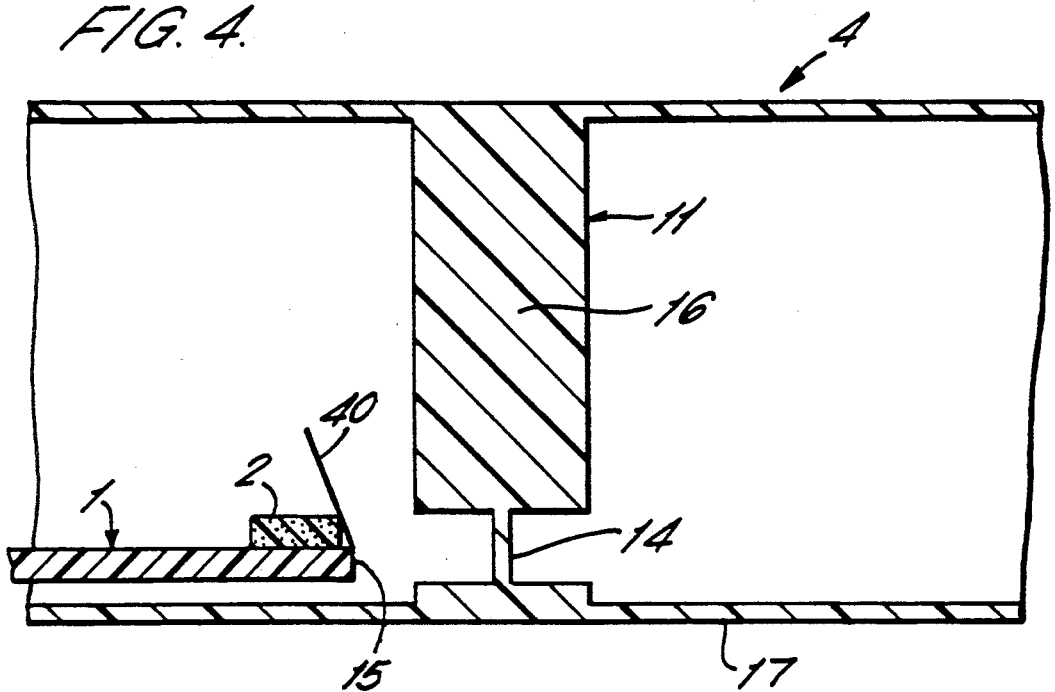
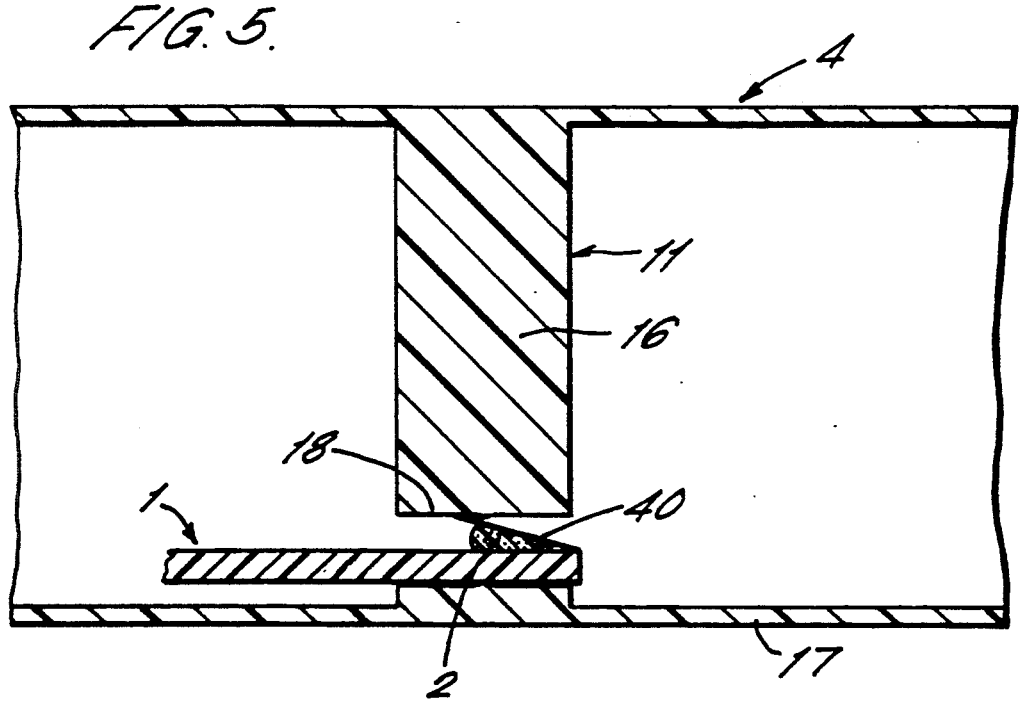

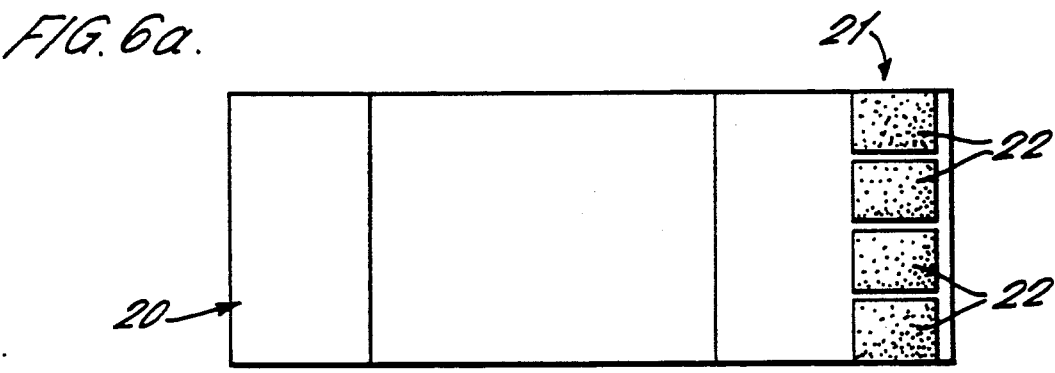
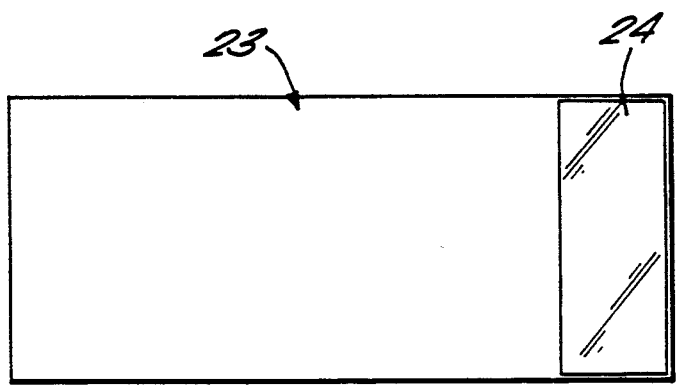
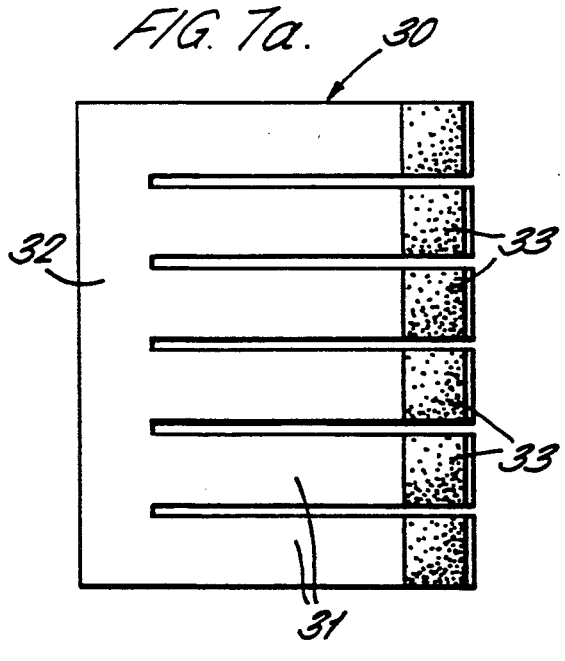
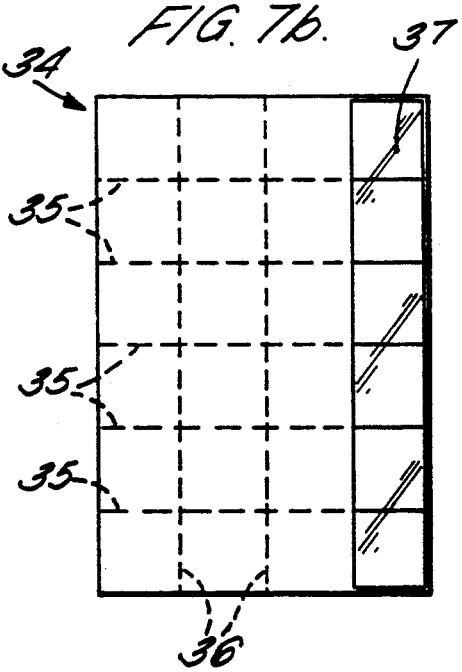

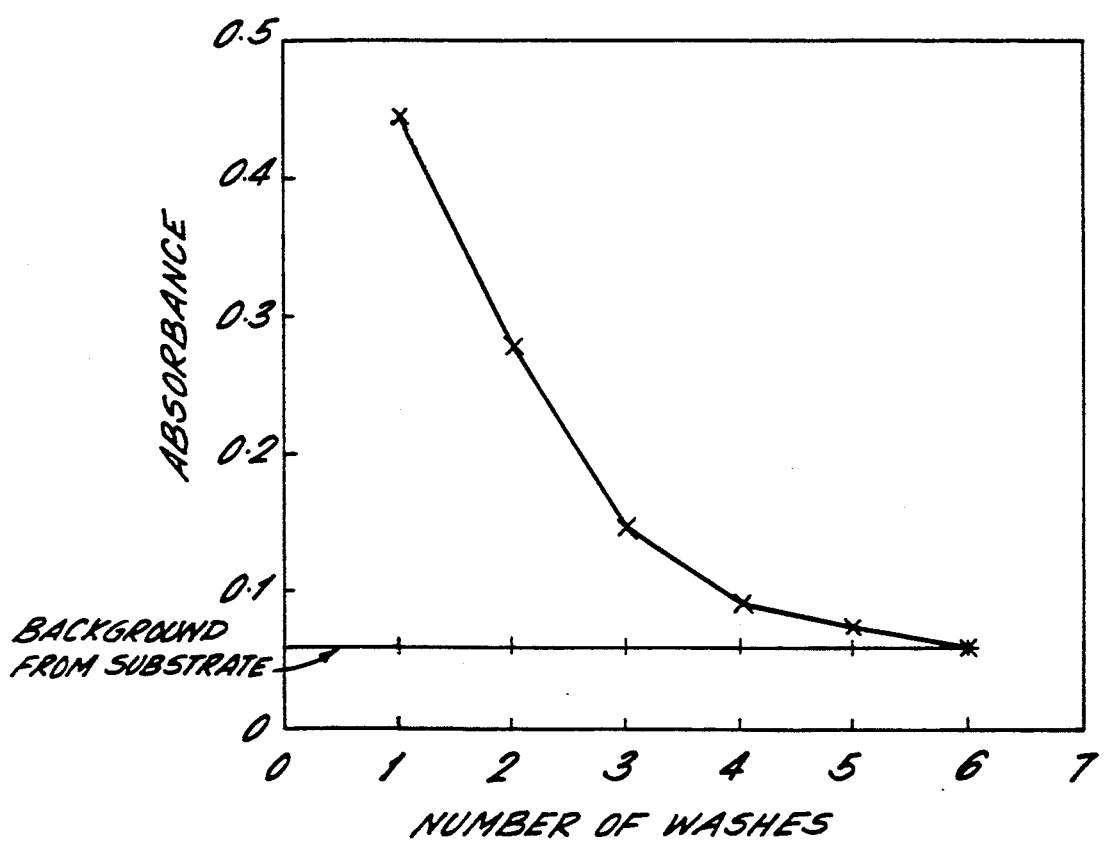

DEVICE FOR ANALYTICAL DETERMINATIONS

The present invention relates to a device for carrying out analytical determinations and, in particular, to a device for carrying out a specific binding assay such as an immunoassay.

There is a great deal of interest in the simplification of analytical techniques to allow the unskilled user to carry out complex assay procedures without error. This is particularly relevant to the field of immunoassays which, in the healthcare field, have been taken out of the clinical laboratory and which are now used in clinics, doctor's offices, veterinary surgeries and even beside the patient or animal. This has been made possible by the introduction of non-isotopic labels, such as enzymes which can give coloured end-points that may be interpreted visually, or measured in a simple instrument. In addition new formats have been devised to simplify greatly the liquid handling of these assays, examples include the immunoconcentration device of Hybritech, U.S. Pat. No. 4,376,110, the inert porous medium of American Hospital Supply Corporation, PCT W082/02601, the concentrating zone method of Syva Company EP-A-0,046,004 and the absorbent matrix pad of Bagshawe, U.S. Pat. No. 3,888,629. In these assay devices the specific binding reactions such as antibody/antigen interactions take place in an absorbent matrix or membrane which is in contact with a quantity of material which acts as an absorber of liquids. In use the sample is applied to the matrix or membrane, further reagents are added, followed by a wash and the addition of an enzyme substrate (when an enzyme label is used). The disadvantage of this type of immunoassay format is that the reagents must be supplied separately i.e. for a manual assay the conjugate, wash buffer and enzyme substrate are made available in dropper bottles containing sufficient fluid to carry out a number of assays. For an assay carried out in an instrument these reagents must be added by complex pipetting methods. These separate reagents increase the complexity of the assay and introduce the possibility of error by an unskilled user introducing reagents in the wrong order or, in an automated device, greatly increase the complexity of the instrument.

Other immunoassay devices have been proposed that use an absorbent or non-absorbent dip-stick to which antibodies have been immobilized e.g. Unilever, EP-A-0,042,755, and Becton Dickinson and Company EP-A-0,194,789. In these devices the sample is contacted with the dip-stick, followed by the further addition of labelled reagents, a wash and the final addition of enzyme substrate (if an enzyme label is used) or the measurement of other labels by various means. The disadvantage of such a system is that the reagents must be added to containers into which the stick is dipped and a separate washing station such as a domestic sink may be required.

GB-A-2073416 describes a two-piece telescoping cylinder unit forming a disposable container for a swab tip and a liquid culture medium. A conical plug seals the liquid from the swab but when the telescoping part are pushed together the plug pivots so that the seal is broken and the liquid culture medium can come into contact with the swab.

EP-A-0206166 describes a test vial comprising a sealed chamber which contains a fluid medium and an open chamber which is external to the sealed chamber and supports the test article. A barrier separates the sealed and open chambers. The vial is equipped with means to penetrate the barrier and inject the test article into the fluid medium.

We have now developed a device for carrying out analytical determinations that contains all of the necessary reagents and wash solution to carry out biological assay or chemical analysis within the device.

According to the present invention there is provided a device for carrying out an analytical determination which comprises a plurality of separate discrete chambers which contain, successively, the reagents required to perform the desired analytical determination, the reagent chambers being separated one from another by a separation means which, in use, is ruptured or opened wherein the device comprises a sample transport body having a sample collection area located thereon;

wherein the reagent chambers are formed in the body portion of an assay cassette which body portion is closed at one end and has an inlet at the other end for the insertion of the sample transport body whereby the sample for analysis is carried to the reagent chambers, the separation means between the reagent chambers, in use, being ruptured or opened by the transport body;

and wherein a signal detection chamber is formed in the body portion of the assay cassette adjacent to the closed end thereof, the signal detection chamber being separated from the final reagent chamber by a separation means which, in use, is ruptured or opened by the transport body.

Each assay cassette is self-contained and requires only the insertion of the sample transport body therein, followed by a simple mechanical manipulation, to complete the assay. The assay or analysis result is visible to the operator if a colorimetric end-point is chosen and, if the sample is also metered, the concentration of the unknown material in the sample may be determined by reference to calibrators or controls which are run simultaneously during the assay. This determination may be carried out visually for a qualitative or semi-quantitative result, or a measuring instrument may be used in a transmission or reflectance mode to give a quantitative result. As further alternatives electrochemical labels may be chosen such as those described by Sereno in EP-A-0,142,301 or radioactive, chemiluminescent or fluorescent labels may be employed. The basic design principle of the assay cassette is applicable to many areas of analysis and the substitution of appropriate reagents will permit both biochemical and chemical analyses to be carried out by an unskilled operator.

The device of the present invention consists of two components; the sample transport body and the assay cassette itself. The sample transport body may comprise a plastic sheet, for example a sheet of methylmethacrylate, polystyrene, nylon or cellulose acetate. The sample transport body has a sample collection area located thereon. In an immunoassay, a specific binding agent such as an antibody or an antigen is immobilised on the sample collection area. The specific binding agents may be directly coupled to the plastic surface using established methods such as passive adsorption or covalent linking. They may be bound to an absorbent membrane or pad of nylon, polyurethane or polyether foam, or cellulose or other compressible material, by passive adsorption or covalent binding. They may be coupled to particles for example of polystyrene or dextran which are held in place by an absorbent material. In the case of direct coupling to the plastic surface it is desirable to cover the surface with a layer of absorbent material. In all three cases described the sample is pipetted or added without measurement to the sample collection area and taken up by the absorbent material. Excess fluid if any, remains on the surface. The sample for an immunoassay may be, for example, urine, whole blood, serum or plasma.

In other areas on the sample transport body both calibrators and controls may be introduced during manufacture and they may be protected from the sample which is to be assayed by a removable covering. In a further modification a filtration layer or layers can be incorporated as the top layer on the sample transport body to remove particles, such as red blood cells, before they reach the antibody layer. The filtration layer may contain antibodies raised against red blood cells to assist in their removal.

The sample transport body containing the sample is then simply pushed into the assay cassette to complete the immunoassay. The assay cassette comprises a series of discrete reagent chambers which for a particular type of immunoassay would be, successively a wash chamber, a conjugate chamber, a further series of wash chambers and the signal detection chamber. Alternatively, if the first wash is not required the reagent chambers for the particular immunoassay being carried out would be successively, a conjugate chamber, a series of wash chambers and the signal detection chamber. Certain chambers in the assay cassette may be left empty in order to ensure a more efficient removal of liquid reagents from the sample collection area. The signal detection chamber may be filled with reagent, for example an enzyme substrate or it may be left empty if a measurement of fluorescence or radioactivity is to be made. If desired, the sample transport body may be marked or calibrated so that the operator is assisted in carrying out the assay correctly. For example the sample transport body may be provided with marks which will indicate to the operator that the sample transport body is located in a particular reagent chamber. The operator may also be reminded of the time for which the sample transport body should remain in that particular chamber.

It will be understood that although the sample transport body may be used in an immunoassay as described above it may also be used to sample other liquids such as milk, fermentation broth, water from a river, lake or sea in order to effect an appropriate analysis thereon. Alternatively, the sample transport body may be used to sample air by an atmospheric aerosol or particle suspension being drawn onto an absorbent matrix on the sample transport body by suction or by use of a venturi.

In a DNA probe assay, the assay cassette provides a considerable simplification of the analytical procedure. The sample transport body is adapted to take up a sample containing DNA, this can be blood or a tissue swab or other biological fluid containing cells or viruses with a DNA or RNA content. The sample may also be taken from a culture of bacterial cells. The assay cassette's internal arrangement of chambers would be, successively a cell lysis, or DNA or RNA extraction chamber with the option of external sonication or heating to assist in sample disruption, a chamber containing a labelled probe, the label may be radioactive, fluorescent, chemiluminescent or a hapten such as biotin to which an avidin/enzyme conjugate can bind, a series of wash chambers to remove excess probe and a signal detection chamber. Alternatively, if the DNA or RNA has already been purified from the sample material before adding to the sample transport body, the first chamber for cell lysis or extraction can be omitted. In these examples, the DNA or RNA from the sample may become bound specifically or non-specifically to the sample transport body. In a further example of a DNA probe assay conducted in the assay cassette, one or successive chambers may contain a heat soluble DNA polymerase, such as that purified from Thermus aquaticus, and also oligonucleotide or polynucleotide primers and nucleotide triphosphates. The application of multiple external heating and cooling cycles to the assay cassette will permit the amplification of the sample DNA according to the method described by Cetus in U.S. Pat. No. 4,683,195. The containment of these DNA amplification steps within the assay cassette ensures that the very large quantities of DNA that can be generated by the polymerase chain reaction method of Cetus remain sealed within the chambers and cannot escape to the external environment. In this way the contamination of laboratory areas, by amplified DNA sequences, which is a growing hazard, can be avoided.

There is considerable interest in automating the complex and time consuming immunoassay and DNA probe procedures. One way in which this has been accomplished, so far, is to retain existing assay formats, such as test-tubes, microtitre wells or the more sophisticated solid phase materials such as cellulose coated magnetic particles and to build a complex mechanical device with multiple functions such as transport, reagent pipetting, washing and detection reagent addition. The assay cassette format offers an alternative route to automation. Since the cassette is entirely self-contained and all reagents are incorporated during manufacture there is no requirement for measured reagent addition or wash steps. After adding the sample to the smple transport body, the instrument completes the assay by simply pushing the sample transport body into the assay cassette until the absorbent area has fully penetrated the signal detection chamber. An assay cassette may be used with standard antigen solutions to calibrate the instrument, or calibrators and controls can be incorporated into each assay cassette from which the instrument can construct a calibration curve.

The assay cassette may also incorporate a sample metering zone which is provided in the body portion adjacent the inlet. The sample metering zone preferably includes a wad of an absorbent material, such as cotton wadding or polyurethane foam, positioned adjacent the inlet, whereby excess sample fluid, if any, is removed from the sample transport body. The sample metering zone will generally be separated from the first reagent chamber by a separation means which, in use, is ruptured or opened by the example transport body.

The separation means which separate the reagent chambers one from another and from the sample metering zone and from the signal detection chamber are ruptured or opened by the sample transport body which is inserted into the assay cassette. The separation means may be, for example, a one-way valve or a plastic film sealed across a window, or a zone of weakness formed in the wall separating the chambers from one another which is ruptured by pressing the sample transport body thereagainst. It will be understood that a single assay cassette may be provided with more than one type of separation means if this is desired.

The signal detection chamber is preferably provided with at least one transparent wall or with a window so that the signal indicating the analytical result may be measured optically by means of an appropriate measuring instrument. The signal detection chamber may also have a different shape to that of the preceding chambers in order to facilitate signal measurements.

In order to seal the sample transport body into the assay cassette at the end of the analytical determination, and thus to prevent the leakage of reagents from the assay cassette, the sample transport body may either be made progressively thick so that, in use, it provides a seal at the first dividing wall, or a flange may be moulded at the end thereof remote from the sample collection zone which is adapted to locate a recess formed in the inlet end of the body portion of the cassette.

In another embodiment of the invention the device may be adapted for the parallel processing of a particular sample and calibrators or controls, or it may be used for the parallel processing of a number of samples from the same or different patients or animals. The sample transport body and the assay cassette are extended laterally to provide a number of further areas on the sample transport body which can have either control materials introduced therein during manufacture or control materials added at the same time as the sample or further sample collection areas. The control areas may be protected from the sample to be analysed by a removable cover which can either be removed by the operator prior to carrying out the analysis, or may be automatically peeled off by means provided in the assay cassette as of the sample transport body is inserted therein. The analytical determination is effected in the same way as that already described and the sample area may then be compared with the control or calibrator areas on completion of the analysis.

Alternatively, the assay cassette may be further subdivided by walls that run parallel to the movement of the sample transport body within the cassette. The sample transport body then has a plurality of limbs for carrying samples, calibrators or controls, as desired. This type of device may be used for carrying out multiple analytical determinations.

Accordingly, the present invention provides a device for carrying out a plurality of analytical determinations which comprises a plurality of separate discrete chambers which contain, successively, the reagents required to perform the desired analytical determinations, the reagent chambers being separated one from another by a separation means which, in use, is ruptured or opened
  wherein the device comprises a sample transport body having a plurality of limbs, each limb having a sample collection area or an area for the transport of a control or calibrator located thereon,
  wherein at least one longitudinal dividing wall is formed in the body portion of an assay cassette to divide the body portion into a number of separate analytical compartments;
  wherein the reagent chambers are formed in the body portion, which body portion is closed at one end and has a single inlet or a plurality of inlets at the other end of the insertion of the limbs of the transport body, whereby the samples for analysis are carried to the reagent chambers, the separation means between the reagent chambers, in use, being ruptured or opened by the limbs of the transport body;
  and wherein a plurality of signal detection chambers are formed in the body portion of the assay cassette adjacent to the closed end thereof, the signal detection chamber in a particular analytical compartment being separated from the final reagent chamber of that analytical compartment by a separation means which, in use, is ruptured or opened by a limb of the sample transport body.

The present invention will be further described with reference to the accompanying schematic drawings, in which:

FIG. 1b is a cross-sectional view of the sample transport body of FIG. 1a;

Figure 2:
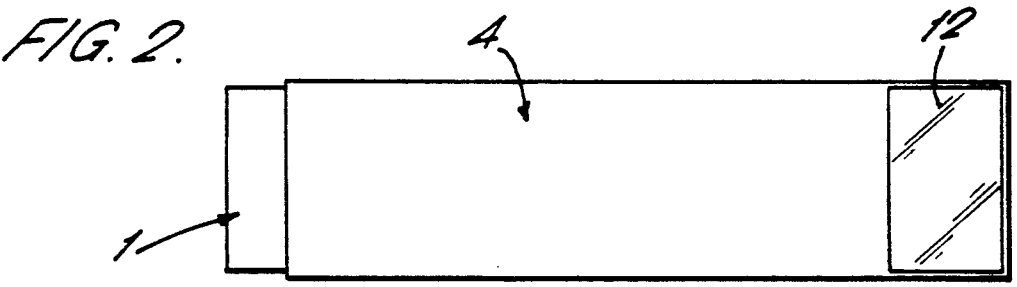
Figure 3A:
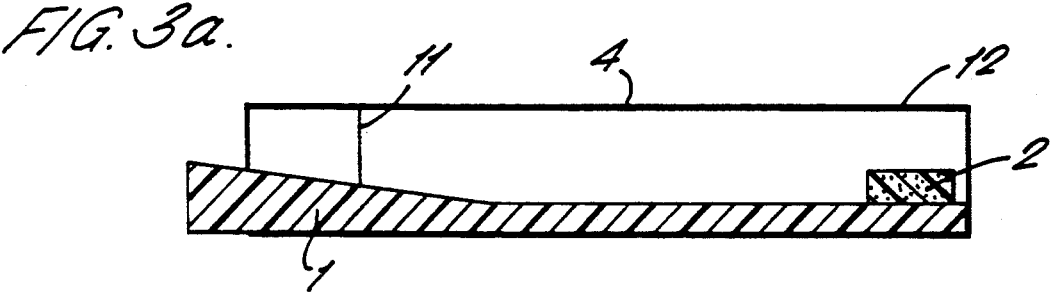
Figure 3B:
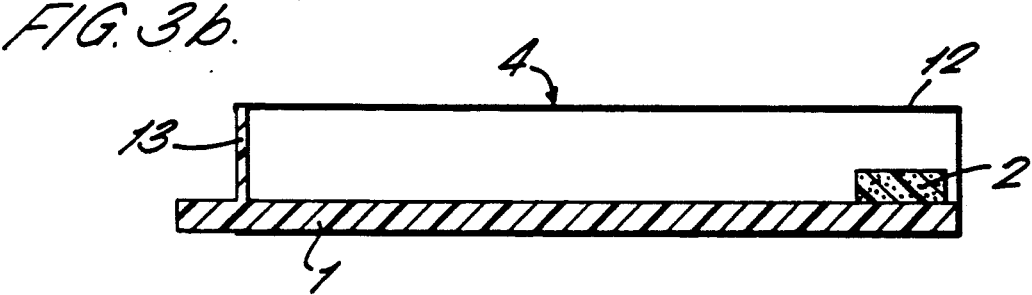

FIG. 2 illustrates the sample transport body located in the assay cassette at the end of the analysis, FIGS. 3a and 3b illustrate two ways in which the sample transport body may be sealed in the assay cassette, FIG. 4 is a cross-sectional view on an enlarged scale of a dividing wall separating two chambers of the assay cassette, FIG. 5 is a cross-sectional view on an enlarged scale of the dividing wall of FIG. 4 with the sample transport body passing therethrough, and FIGS. 6a and 6b illustrate a sample transport body and assay cassette, respectively, intended for the parallel processing of a sample and calibrators or controls.

FIGS. 7a and 7b illustrate a sample transport body and assay cassette, respectively, intended for the parallel processing of a sample and calibrators or controls, or for the parallel processing of a number of samples.

FIG. 8 illustrates the results from a washing experiment to remove alkaline phosphatase from the sample transport body during passage through the assay cassette.

Figure 9:
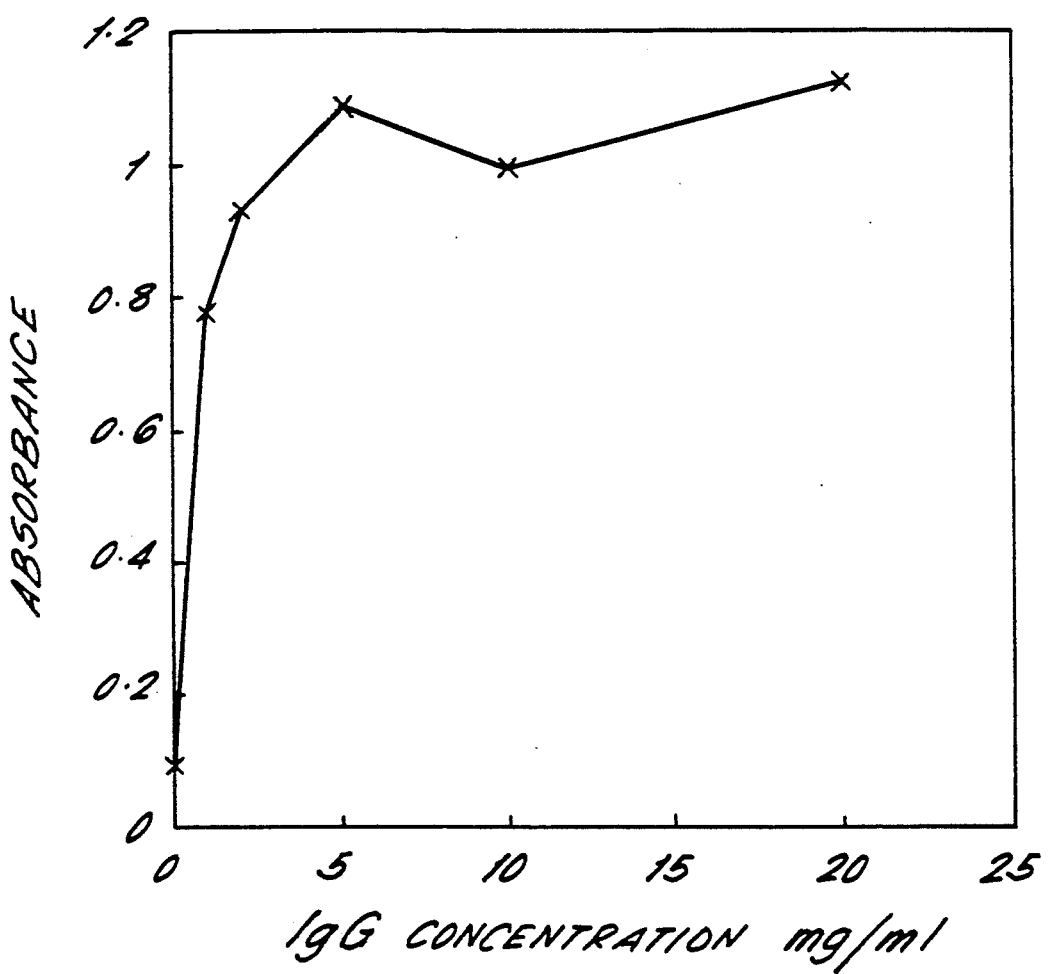

FIG. 9 illustrates the results from an immunoenzymometric assay for human IgG carried out using the assay cassette.

Figure 1A:
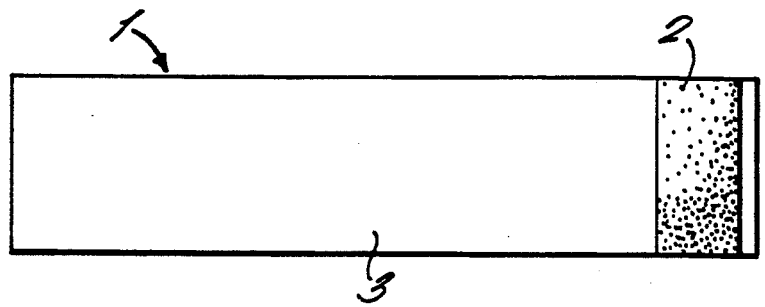
FIG. 1a is a plan view of the sample transport body of the device of the invention.
Figure 1B:
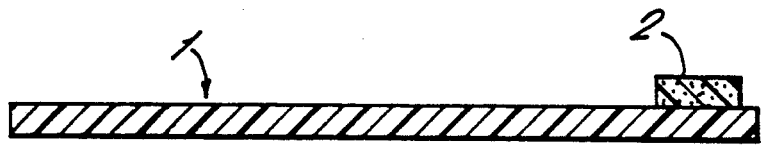
Figure 1C:
FIG. 1c is a cross-sectional view of an alternative sample transport body configuration.

Referring to the Drawings, FIGS. 1a, 1b and 1c illustrate the sample transport body 1. The sample transport body is an elongate plastics member to which an absorbent material 2 is bonded at one end thereof. The absorbent material 2 extends across one surface 3 of the transport body and provides a volume of approximately 1.0 cubic centimetres as the sample collection area. The rest of the sample transport body is exposed and is intended to be held in the hand. FIG. 1c illustrates an alternative configuration where the absorbent material is covered by a protective flap 40 which is bonded to the end of the sample transport body, or is attached to the end of the sample transport body before, or during its passage through the assay cassette.

Figure 1D:
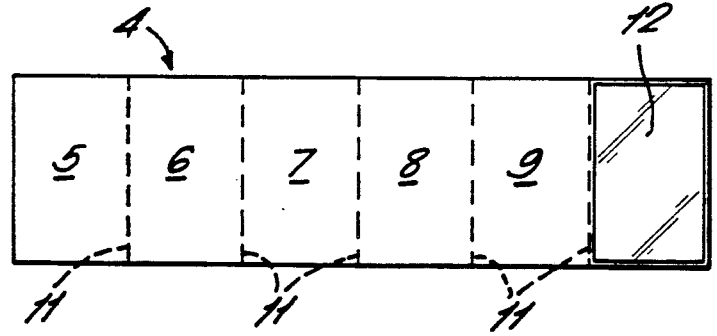
FIG. 1d is plan view of the assay cassette of the device of the invention.
Figure 1E:
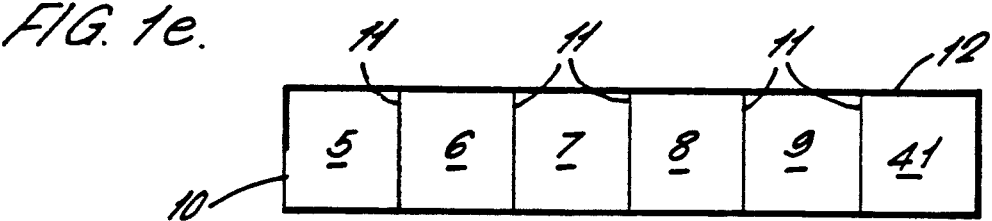
FIG. 1e is a cross-sectional view of the assay cassette of FIG. 1d.

FIGS. 1d and 1e illustrate schematically the assay cassette which is used in the invention. The assay cassette 4 is of elongate construction and formed from a suitable plastics material. The assay cassette has a series of chambers 5, 6, 7, 8, 9 and 41 formed therein. The first chamber of the series, chamber 5, is provided with an inlet 10 through which, in use, the sample transport body is inserted. The various chambers are separated one from another by internal dividing walls 11 which are represented in the schematic diagrams by a series of dotted lines. Chamber 41 is provided with an observation window 12 through which the sample transport body can be viewed after it has been fully inserted into the assay cassette.

Chamber 5 comprises a sample metering zone which generally contains a material such as cotton wadding or a polyurethane foam adjacent entry slot 10 which is intended to wipe excess sample, if any, from the top surface of the absorbent matrix 2 bonded to sample transport body 1. Chamber 6, 7 and 8 contain reagent fluids for the appropriate analytical determination which is being carried out.

FIG. 2 illustrates the combination of the assay cassette 4 and the sample transport body 1 after the sample transport body 1 has been fully inserted into the assay cassette 4. The sample collection area 2 of the sample transport body 1 is visible through observation window 12. It will be noted that the sample transport body 1 projects from the end of the assay cassette.

FIGS. 3a and 3b illustrate schematically two ways in which the leakage of fluid from the cassette can be prevented after the completion of the analysis. As shown in FIG. 3a in cross-section the sample transport body 1 increases progressively in thickness towards the end which is distant from the sample collection area. In this manner the sample transport body 1 provides a seal at the first dividing wall 11 of the assay cassette 4. The remaining dividing walls in cassette 4 are not shown. As shown in FIG. 3b, the sample transport body 1 is provided with an upstanding flange 13 which is adapted to locate in a co-operating recess formed in the inlet end of the assay cassette 4.

FIGS. 4 and 5 illustrate, on an enlarged scale, a dividing wall 11 of the assay cassette 4 before and after it has been ruptured by the sample transport body 1, which in this diagram has been fitted with a protective flexible flap 40 over the absorbent material. As shown in FIG. 4 the dividing wall 11 has a zone of weakness 14 where the end of the wall abuts the lower surface of assay cassette 4. Movement of sample transport body 1 horizontally causes the tip of the sample transport body 15 to meet the zone of weakness 14 and further movement in the horizontal direction will cause the dividing wall to rupture. FIG. 5 illustrates the sample transport body penetrating through the ruptured wall into the next reagent chamber. The thicker portion 16 of the dividing wall 11 remains intact during this procedure and acts as a guide to keep the sample transport body 1 pressed close to the lower surface 17 of assay cassette 4. It will be understood that the sample transport body 1 may extend across the full width of the assay cassette, or it may span only a part of this distance in which case a part only of the dividing wall 11 need have the required zone of weakness. As shown in FIG. 5 the clearance between the lower surface 17 of the assay cassette 4 and the tip 18 of ruptured dividing wall 11 is such that the sample collection area 2, composed of absorbent material, is compressed during the passage of the sample transport body 1 through the dividing wall 11 by the protecting flap 40. This is intended to facilitate the analysis by expelling the majority of one reagent from the sample collection area 2 before the sample collection area 2 is exposed to the reagent in the next successive chamber. If desired, additional projections (not shown) may be included in each reagent chamber to compress and thereafter release the sample collection area 2 in order to ensure efficient liquid flow therethrough.

There are various ways in which the rupturable walls and separate reagent chambers of the assay cassette may be constructed. Preferred manufacturing routes include the moulding of the interior walls and side walls as a complete unit, with the subsequent addition of top and bottom walls by ultrasound welding or adhesive. Alternatively, a moulding comprising side, interior and bottom walls is produced, with the open windows in the interior walls being sealed by subsequently placing a plastic film inside each chamber, the top wall being added by ultrasound welding or adhesive after filling the chambers with the liquid reagents. A third preferred manufacturing route is to produce the chambers as discrete units, approximately as cubes and to cover an open face of the unit with plastic film before filling with liquid reagent. The discrete chamber unit is then sealed by applying a plastic film to the remaining open face. The complete assay cassette is then manufactured by butting successive discrete chamber units in a longitudinal array and holding them in position with a plastic clip or by sealing in a surrounding plastic tube.

FIGS. 6a and 6b illustrate schematically an assay device which is intended for the parallel processing of a particular sample and calibrators or controls. A sample transport body is illustrated generally at 20. This sample transport body 20 is of a similar construction to that of the sample transport body described with reference to FIG. 1 and it comprises a sample collection area 21. Control and calibrator areas 22 are also provided on the sample transport body 20. The assay cassette 23 which is illustrated in FIG. 6b has an elongated observation window 24. The assay cassette 23 is provided internally with the features as described with reference to assay cassette 4, but these are not shown. On completion of the analysis the sample area 21 may be compared with the control and calibrator areas 23 through observation window 24.

FIGS. 7a and 7b illustrate schematically an assay device which is intended for the parallel processing of a sample and calibrators or control samples, or for the parallel processing of a number of samples either from the same or different patients or animals. A sample transport body is illustrated generally at 30. This sample transport body 30 has a pluality of limbs 31 which are joined together by a bridge 32. The limbs 31 and bridge 32 are formed from a single sheet of a moulded plastics material. At the end of each limb 31 distant from bridge 32 areas 33 are provided. These areas 33 are intended either as sample areas or for calibrators and controls as desired, depending upon the particular analysis being performed. The assay cassette 34 which is illustrated in FIG. 7b has longitudinal dividing walls 35 and transverse dividing walls 36 provided therein. The transverse dividing walls 36 are rupturable or openable by the limbs 31 of transport body 32. The assay cassette 34 is also provided with an observation window 37 so that on completion of the analysis the various areas 33 may be compared therethrough. The individual reagent chambers are kept separate from the reagent chambers on either side thereof. With this particular type of device containing rigid longitudinal dividing walls it is possible to effect multiple analyses. In an immunoassay, the simultaneous assay of related substances such as thyroid stimulating hormone, thyroxine and triiodothyronine, which are often all measured when the thyroid status of a patient is assessed, could be carried out. In biochemical analysis a blood biochemistry series of tests consisting of, for example, the assay of glucose, total protein, sodium, potassium, creatinine and cholesterol could be carried out simultaneously on a patient's sample in a single assay cassette of this type.

The device described above with reference to FIGS. 1 to 5 of the accompanying Drawings is described further in the Examples below with reference to carrying out an immunoassay therein.

EXAMPLE 1

A key feature of the assay cassette of the invention is the efficient separation of free from bound labelled reagent in an immunoassay or DNA probe assay. An experiment was carried out to prove that a typical enzyme label, such as alkaline phosphatase could be readily removed from the absorbent area of the sample transport body. To the end of a sample transport body constructed from methyl methacrylate of dimensions 15 cm $\times$ 2 cm $\times$ 2 mm was bonded a piece of high density fully reticulated polyurethane foam of dimensions 1 cm $\times$ 1 cm $\times$ 1 cm. Then, 50 $\mu$l of a solution of alkaline phosphate in a 100 mM tris buffer pH of 7.5 at a concentration of 10 $\mu$g/ml was added to the foam and the sample transport body was pushed gently through a series of chambers in an assay cassette constructed from methyl methacrylate; each chamber having dimensions of 2 cm $\times$ 1 cm $\times$ 1 cm, and separated by a rupturable wall comprising a 5 $\mu$m thick film of plasticised polyvinyl chloride stretched across a window cut in the dividing walls. The chambers were filled with 2.5 ml of a 100 mM tris buffer pH of 7.5 containing 0.1% (v/v) polyoxyethylenesorbitan monolaurate and 0.1% (w/v) sodium azide. After completing the procedure a sample of 100 $\mu$l was taken from each chamber and added to a spectrophotometer cuvette containing 0.9 ml of a solution containing 2 mg/ml p-nitrophenol phosphate in 100 mM diethanolamine buffer having a pH of 9.5. The rate of appearance of p-nitrophenol was measured at 405 nm and was taken as an indication of enzyme activity. FIG. 8 shows the amount of enzyme activity found in each successive chamber of the assay cassette after the sample transport body had passed through. The results show that after passing through 6 chambers the amount of alkaline phosphatase remaining in the foam had been reduced to zero.

EXAMPLE 2

An immunenzymometric assay for human IgG was carried out in the assay cassette described in Example 1. In this case the chambers were filled successively with labelled antibody conjugate, followed by five wash chambers and a signal detection chamber filled with enzyme substrate, 2 mg/ml p-nitrophenol phosphate in a 100 mM diethanolamine buffer having a pH 9.5. The enzyme-labelled conjugate comprised a rabbit anti-human IgG polyclonal antibody linked to alkaline phosphatase using a glutraldehyde coupling procedure. The conjugate was dissolved in a 100 mM tris buffer having a pH of 7.5 containing 0.5% (w/v) casein, 1 mM magnesium chloride and 0.04 (w/v) thimerosal at a conjugate concentration of 4 $\mu$g/ml. The same anti-human IgG used in the conjugate was also immobilised to high density polyurethane foam of the fully reticulated type by a passive adsorption process involving saturating the foam with a solution of antibody at 5 $\mu$g/ml in a 200 mM sodium carbonate buffer having a pH of 9.0 and incubating for 16 hours at 37° C.

After coating with antibody the foam was washed three times with a solution containing 100 mM tris buffer pH 7.5 and 0.5% (w/v) casein and was dried in air at room temperature (22° C.). A 1 cm $\times$ 1 cm $\times$ 1 cm block of the antibody coated foam was bonded to the end of the sample transport body of dimensions 15 cm $\times$ 2 cm $\times$ 2 mm. To carry out the assay, an aliquot of 50 $\mu$l of a solution of 100 mM tris buffer pH of 7.5 containing various concentrations of human IgG was pipetted onto the foam block and the sample transport body was immediately pushed gently through the successive chambers in the assay cassette, without pausing. The dimensions of the assay cassette and the composition of the wash buffers were as described in Example 1. The colour development in the signal detection chamber was allowed to continue for 10 minutes before a measurement was made at 405 nm. FIG. 9 shows a dose-response curve for a series of individual human IgG assays with increasing concentration of antigen. This experiment shows that the assay cassette format provides a rapid and quantitative assay for human IgG. The speed with which this assay could be carried out is due to the very high surface area within the high density reticulated foam which provides rapid reaction kinetics. It is also advantageous to have a mechanically driven flow of liquid reagents through the foam to provide a further acceleration in the reaction.

Variations on the assay cassette design used in the present invention can be introduced depending upon the assay sequence of reagents required to carry out the particular analytical determination. It is only necessary to adjust the number of reagent chambers and the reagents contained within each successive chamber, as required.

The device of the present invention for carrying out analytical determinations may be used in many areas of analysis and it is not intended that its application be restricted only to the area of immunoassay or DNA or RNA assay. For example, the reagent chambers may be filled with liquid reactants for total protein, carbohydrate or fat assays when the nutritional status of feed materials is to be assessed; or alternatively phosphate, nitrate or other pollutant measurements may be made on freshwater supplies using the appropriate reagents. There are many more applications that can be envisaged for the device of the invention where the important features of automatic sample metering, simultaneous processing of sample and calibators or controls and integral reagent chambers provide the unskilled user with a reliable and easy to use assay system.

I claim:

1. An assay cassette device for carrying out an analytical determination including a body portion containing a plurality of separate discrete reagent chambers each containing, successively, a reagent required to perform the desired analytical determination, the reagent chambers being separated one from another by a separation means which, in use is ruptured or opened, a sample transport body having a sample collection area located thereon, the sample collection area having a specific binding agent immobilized thereon;

said reagent chambers formed in the body portion of an assay cassette, the body portion being closed at one end and has an inlet at the other end for insertion of the sample transport body whereby the sample for analysis is carried to the reagent chambers; said separation means between the reagent chambers, in use, being ruptured or opened by the transport body; and a signal detection chamber formed in the body portion of the assay cassette adjacent to the closed end thereof, the signal detection chamber being separated from the final reagent chamber by a separation means which, in use, is ruptured or opened by the transport body and said signal detection chamber being provided with a transparent wall.

2. A device as claimed in claim 1 wherein the assay cassette incorporates a sample metering zone provided in the body portion adjacent the inlet.

3. A device as claimed in claim 2 wherein the sample metering zone includes a wad of an absorbent material positioned adjacent the inlet.

4. A device as claimed in claim 1 wherein at least one of said separation means is a one-way valve.

5. A device as claimed in claim 1 wherein at least one of said separation means comprises a zone of weakness formed in the wall or walls separating the chambers.

6. A device as claimed in claim 1 wherein at least one of said separation means comprises a plastic film separating the chambers.

7. A device as claimed in claim 1 wherein the sample collection area comprises an absorbent body bonded to one end of the sample transport body.

8. A device as claimed in claim 8 wherein the absorbent body is covered by a protective flap.

9. A device as claimed in claim 1 wherein the sample transport body has a flange formed at the end thereof remote from the sample collection area which is constructed so as to be located in a recess formed in the inlet area of the body portion of the assay cassette.

10. A device as claimed in claim 1 wherein the sample transport body has a progressively increasing thickness towards the end thereof remote from the sample collection area.

11. A device as claimed in claim 1 wherein the sample transport body is provided with markings in order to assist the operator in carrying out the analysis.

12. A device as claimed in claim 1, including means for the parallel processing of a sample and calibrator and/or controls.

13. A device as claimed in claim 12 wherein the sample transport body has areas formed thereon which are impregnated with the calibrators and/or controls and an area which is adapted for the collection of the sample to be analysed.

14. A device as claimed in claim 13 wherein the pre-impregnated areas are protected from the sample to be analysed by means of a removable cover.

15. A device as claimed in claim 7 wherein the absorbed body for the collection of the sample to be analysed is covered with a peel-off filter layer to remove unwanted materials from the sample before it contacts the absorbent material.

16. A device as claimed in claim 1, wherein the reagent chambers contain the reagents required to carry out a particular immunoassay.

17. A device as claimed in claim 1, wherein the reagent chambers contain the reagents required to carry out a DNA or RNA probe assay.

18. An assay cassette device for carrying out a plurality of analytical determinations including a body portion containing a plurality of separate discrete reagent chambers each containing successively, a reagent required to perform the desired analytical determinations, the reagent chambers being separated one from another by a separation means which, in use, is ruptured or opened a sample transport body having a plurality of limbs, each limb having at least one sample collection area and optionally at least one area for the transport of a control and/or optionally at least one area for the transport of a calibrator located thereon, each sample collection area having a specific binding agent immobilized thereon;

at least one longitudinal wall formed in the body portion of an assay cassette to divide the body portion into a number of separate analytical compartments;

said reagent chambers being formed in the body portion, the body portion being closed at one end and has a single inlet or a plurality of inlets at the other end for the insertion of the limbs of the transport body, whereby the samples for analysis are carried to the reagent chambers, the separation means between the reagent chambers, in use, being ruptured or opened by the limbs of the transport body;

and a plurality of signal detection chambers formed in the body portion of the assay cassette adjacent to the closed end thereof, the signal detection chamber in a particular analytical compartment being separated from the final reagent chamber of that analytical compartment by a separation means which, in use, is ruptured or opened by a limb of the sample transport body and each signal detection chamber being provided with a transparent wall.

19. A device as claimed in claim 18 wherein each analytical compartment has a plurality of reagent chambers formed therein.

20. A device as claimed in claim 18 wherein each analytical compartment incorporates a sample metering zone adjacent the inlet thereof.

21. A device as claimed in claim 18 wherein the reagent chambers contain the reagents required to carry out a particular immunoassay.

22. A device as claimed in claim 18 wherein the reagent chambers contain the reagents required to carry out a DNA or RNA probe assay.

* * * * *